United States Patent [19]

Mignani et al.

[11] Patent Number: 5,243,097
[45] Date of Patent: Sep. 7, 1993

[54] PROCESS FOR THE CONTINUOUS BULK PRODUCTION OF ACRYLIC POLYMERS

[75] Inventors: Gerard Mignani, Lyon; Didier Morel, Villiers Sur Orge, both of France

[73] Assignee: Rhone-Poulenc Sante Les Miroirs, France

[21] Appl. No.: 979,344

[22] Filed: Nov. 20, 1992

Related U.S. Application Data

[63] Continuation of Ser. No. 697,924, May 2, 1991, abandoned, which is a continuation of Ser. No. 571,825, Aug. 23, 1990, abandoned, which is a continuation of Ser. No. 894,490, Aug. 11, 1986, abandoned, which is a continuation of Ser. No. 671,879, Nov. 16, 1984, abandoned.

[30] Foreign Application Priority Data

Nov. 18, 1983 [FR] France ............... 83 18391

[51] Int. Cl.$^5$ .......................................... C07C 33/04
[52] U.S. Cl. .......................................... 568/873
[58] Field of Search .......................................... 568/873

[56] References Cited

U.S. PATENT DOCUMENTS

| | | | |
|---|---|---|---|
| 3,940,425 | 2/1976 | Eiter ..................... | 568/873 |
| 4,056,523 | 11/1977 | Close et al. ............ | 568/875 |
| 4,147,672 | 4/1979 | Schulte-Elte et al. ... | 252/522 |
| 4,210,610 | 7/1980 | Sabourin et al. ....... | 568/812 |
| 4,264,467 | 4/1981 | Schulte-Elte et al. ... | 252/522 |
| 4,289,659 | 9/1981 | Schulte-Elte et al. ... | 252/522 |

FOREIGN PATENT DOCUMENTS 775723   5/1957   United Kingdom .

OTHER PUBLICATIONS

Cardiot et al. The Chemistry of Acetylenes Chap. 9 pp. 628–641 (1969).
Eglinton et al. Advances in Organic Chemistry vol. 4, pp. 225–323 (1963).

*Primary Examiner*—Jose G. Dees
*Assistant Examiner*—Joseph Conrad, III
*Attorney, Agent, or Firm*—Morgan & Finnegan

[57] ABSTRACT

Acetylenic derivatives of general formula

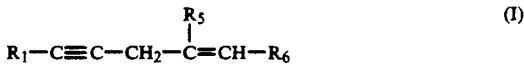

in which $R_1$ denotes a hydrogen atom or a phenyl radical or a radical of general formula

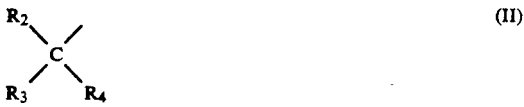

in which $R_2$ and $R_3$, which may be identical or different, denote a hydrogen atom or a saturated or unsaturated aliphatic radical, substituted if appropriate, or form together a cycloaliphatic radical, $R_4$ denotes a hydrogen atom or a saturated or unsaturated aliphatic radical, a hydroxy, alkyloxy, methanesulphonyloxy, benzenesulpnonyloxy or p-toluenesulphonyloxy radical, $R_5$ denotes a hydrogen atom or a saturated aliphatic radical, $R_6$ denotes a hydrogen atom or a saturated or unsaturated aliphatic radical are made by reaction of an acetylenic derivative of general formula

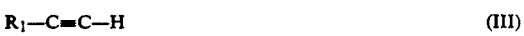

with an allyl derivative of general formula

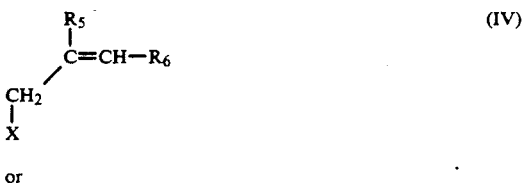

or

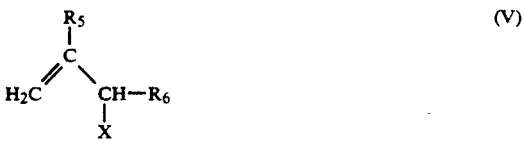

in the presence of a cuprous salt and an anhydrous organic base. The compounds of formula (I) are useful in organic synthesis, in particular in the preparation of the vitamins A and E.

1 Claim, No Drawings

PROCESS FOR THE CONTINUOUS BULK PRODUCTION OF ACRYLIC POLYMERS

This is a continuation of co-pending application Ser. No. 07/697,924, filed on May 2, 1991, now abandoned, which is a continuation of 571,825, filed on Aug. 23, 1990, now abandoned, which is a continuation of Ser. No. 894,490, filed on Aug. 11, 1986, now abandoned, which is a continuation of Ser. No. 671,879 filed Nov. 16, 1984 now abandoned.

This invention relates to the preparation of acetylenic derivatives useful more particularly in the synthesis of vitamins A and E.

It is known in particular from P. Cadiot and W. Chodkiewicz, Chapter 9, page 628 and following, in the book "The Chemistry of Acetylenes" by H. G. Viehe, Marcel Dekker, New York (1969), to condense acetylenic derivatives with allyl halides in an aqueous medium in the presence of a cuprous salt and a base, but this reaction results in a mixture of linear and branched products according to the reaction scheme:

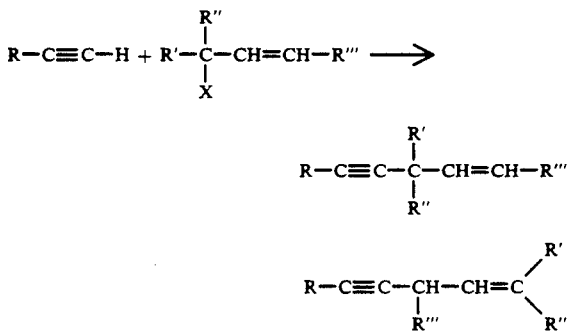

It is also known according to U.S. Pat. No. 4,056,573 to condense methylbutynol with 1-chloro-4-acetoxy-2-methyl-2-butene in the presence of a stoichiometric quantity of a cuprous salt and an organic base which is a primary or secondary amine in an organic solvent such as dimethylformamide when the operation is carried out in a non-aqueous medium, or in the presence of a stoichiometric quantity of cuprous salt and an agent making it possible to buffer the medium such as sodium acetate or sodium phosphate when the operation is carried out in an aqueous medium. However, this condensation takes place with poor yields and it leads to the formation of undesirable by-products.

The present invention provides a new process for preparing acetylenic derivatives of the formula

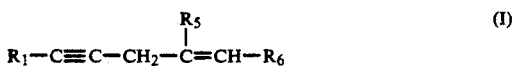

in which:

$R_1$ denotes hydrogen, phenyl, or a radical of formula:

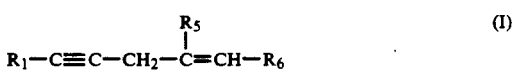

in which $R_2$ and $R_3$, which are identical or different, each denote a hydrogen atom or a saturated or unsaturated aliphatic radical which is unsubstituted or substituted by a 5 or 6 membered cycloaliphatic radical which is saturated or contains one or two double bonds and is unsubstituted or substituted by one or more alkyl radicals of 1 to 4 carbon atoms each, it being understood that at least one of the symbols $R_2$ and $R_3$ is a said saturated or unsaturated aliphatic radical, or $R_2$ and $R_3$ together form a 5 or 6 membered cycloaliphatic radical which is saturated or contains one or two double bonds and is unsubstituted or substituted by one or more alkyl radicals of 1 to 4 carbon atoms each; and $R_4$ denotes a hydrogen atom, a saturated or unsaturated aliphatic radical, hydroxy, an alkoxy radical whose alkyl part has 1 to 4 carbon atoms, an alkyl-carbonyloxy radical whose alkyl part has 1 to 4 carbon atoms, methanesulphonyloxy, benzenesulphonyloxy, or p-toluenesulphonyloxy;

$R_5$ denotes a hydrogen atom or a saturated aliphatic radical; and $R_6$ denotes a hydrogen atom, a saturated or unsaturated aliphatic radical, acetyl, formyl which may be in the form of an acetal radical, hydroxy which may be in the form of an ether or ester, or an alkyloxycarbonyl radical.

In the above and the following, the saturated aliphatic radicals contain 1 to 11 carbon atoms and the unsaturated aliphatic radicals contain 2 to 11 carbon atoms and one or more double bonds and are unsubstituted or substituted by one or more radicals, which may be identical or different, chosen from acetyl, formyl which may be in the form of an acetal radical, hydroxy which may be in the form of an ether or ester, and an alkyloxycarbonyl radical.

Among the compounds of formula (I), those for which $R_1$ is defined as above, $R_5$ denotes a saturated aliphatic radical, and $R_6$ denotes a radical of the formula:

in which $R_7$ denotes a hydrogen atom or a saturated aliphatic radical of 1 to 9 carbon atoms or an unsaturated aliphatic radical of 2 to 9 carbon atoms which is unsubstituted or substituted by one or more radicals, which may be identical or different, chosen from acetyl, formyl which may be in the form of an acetal radical, hydroxy which may be in the form of an ether or ester, or an alkyloxycarbonyl radical, or $R_7$ denotes acetyl, formyl which may be in the form of an acetal radical, hydroxy which may be in the form of an ether or ester, or an alkyloxycarbonyl radical, are new products which form another subject of the present invention.

Preferably, the said unsaturated aliphatic radicals have an isoprenic or polyisoprenic structure.

Those of very particular interest are the compounds of formula (I) in which:

$R_1$ denotes a radical of general formula (II) in which $R_2$ denotes a saturated aliphatic radical containing 1 to 11 carbon atoms or an unsaturated aliphatic radical containing 2 to 11 carbon atoms and one to three double bonds, which is unsubstituted or substituted by a cyclohexyl or cyclohexenyl radical which is unsubstituted or substituted by one or more alkyl radicals of 1 to 4 carbon atoms each, $R_3$ denotes a hydrogen atom or a sataurated aliphatic radical of 1 to 4 carbon atoms, or $R_2$ and $R_3$ together form a cyclohexyl or cyclohexenyl radical which is unsubstituted or substituted by one or more alkyl radicals containing 1 to 4 carbon atoms each, $R_4$ denotes a hydrogen atom or a hydroxy radical, $R_5$ denotes a saturated aliphatic radical of 1 to 4 carbon atoms, and $R_6$ denotes a saturated aliphatic radical of 1 to 11 carbon atoms or an unsaturated aliphatic radical of 2 to 11 carbon atoms which is unsubstituted or substituted by acetyl, formyl which may be in the form of an acetal radical, or hydroxy which may be in the form of an ether or ester.

According to the present invention, the acetylenic derivatives of general formula (I) are obtained by reacting an acetylenic derivative of the formula:

   (IV)

in which $R_1$ is as defined above, with an allylic derivative of the formula:

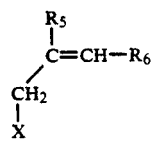   (V)

or

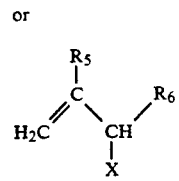   (VI)

in which $R_5$ and $R_6$ are as defined above, and X denotes halogen, methanesulphonyloxy, benzenesulphonyloxy, p-toluenesulphonyloxy radical or a quaternary ammonium radical, the operation being carried out in the presence of a copper (I), i.e. cuprous, derivative and an anhydrous organic base. Using the new process, a linear product is essentially formed whether the allylic derivative used as starting material has the formula (V) or (VI).

The copper derivatives which are used as catalysts are derivatives of copper (I) or of copper (II) which has been reduced beforehand to copper (I).

Suitable copper (I) derivatives include cuprous salts such as CuCl, Cu$_2$O, CuI, CuBr, CuCN, Cu—C≡C—Cu, CuOCOCH$_3$, CuNO$_3$, C$_6$H$_5$—Cu, Cu(CH$_3$COCHCOCH$_3$), (CH$_3$)$_2$C(OH)—C≡C—Cu and copper (I) complexes such as [CuCl(1,5-cyclooctadiene)]$_2$, CuCl [N(C$_2$H$_5$)$_3$]$_3$, CuCl [N(C$_2$H$_5$)$_3$]$_2$, CuBr [N(C$_2$H$_5$)$_3$]$_3$, [CuCl(NCR]$_n$, CuCl pyridine)$_n$ or CuCl(adiponitrile).

Suitable copper (II) derivatives which may be reduced include cupric salts such as CuCl$_2$, CuBr$_2$, Cu(CN)$_2$, Cu(OCOCH$_3$)$_2$, Cu(NO$_3$)$_2$ and copper (II) complexes such as CuCl$_2$(amine)$_n$ or CuCl$_2$(CH$_3$CN)$_2$. When a copper (II) derivative is employed as a precursor of the catalyst based on copper (I), the former is reduced to a copper (I) derivative by the acetylenic compound of general formula (IV), as disclosed by G. Ellington and W. McCrae, Advances in Organic Chemistry, volume 4, page 225 (1963).

The catalyst based on a copper (I) derivative may, if desired, be used in the presence of a co-catalyst which is an ammonium halide such as tetraethylammonium chloride, a phosphonium halide such as tetrabutylphosphonium chloride, or an alkali metal or alkaline earth metal halide. Generally the molar ratio of co-catalyst/catalyst is between 1 and 50, and preferably between 1 and 10.

Generally, a quantity of catalyst based on a cuprous derivative is employed which represents from 0.1 to 20%, and preferably from 1 to 5%, by mol of the allylic derivative of formula (V) or (VI).

Particularly suitable anhydrous organic bases are tertiary amines such as triethylamine, tributylamine, pyridine, lutidine or collidine. Generally 1 to 20 moles, and preferably 1 to 5 moles, of base are used per mole of allylic derivative of formula (V) or (VI).

Generally, the acetylenic derivative of formula (IV) is used in a proportion of 1 to 20, and preferably 1 to 4, moles per mole of allylic derivative of formula (V) or (VI).

The reaction temperature is generally between 20° and 100° C., but it is preferable to operate between 40° and 80° C., and the reaction is continued to complete conversion of the allylic derivative of formula (V) or (VI).

It is particularly advantageous to operate the process of the present invention in such a way that the catalyst may be recycled. At the end of the reaction, the reaction mixture consists essentially of a homogeneous liquid containing the final product of the reaction, starting products which may not have reacted, the organic base (e.g. triethylamine) employed as solvent, the dissolved copper catalyst, and a solid precipitate consisting essentially of the organic base salt (e.g. triethylamine hydrochloride).

In order to recover the copper complex for it to be re-used in a subsequent operation, the reaction mixture may be treated in the following manner:

after separation of the solid fraction from the reaction mixture by filtration, the filtrate obtained is concentrated under reduced pressure so as to obtain a homogeneous oily mixture consisting of the reaction products, starting materials which may not have reacted, and the soluble form of the copper catalyst, the oily mixture obtained is treated with an organic solvent which does not dissolve the complexes of the organic base with the copper catalyst, such as an aliphatic hydrocarbon (e.g. pentane, hexane), a cycloaliphatic hydrocarbon (e.g. cyclohexane), or an aliphatic ether (e.g. diethyl ether) so as to obtain an extract containing essentially the solvent and the organic products (reaction products and unreacted starting materials) and small quantities of copper, and a raffinate containing essentially the catalytic copper complex and unextracted organic products. The treatment of the raffinate with the organic solvent may be repeated several times. The raffinate finally obtained may be employed for carrying out a subsequent operation. Generally, the degree of catalyst recovery is close to 90%.

The acetylenic derivatives of formula (I) obtained by the process of the present invention may be isolated from the reaction mixture or from the extracts with a suitable solvent and purified by the application of conventional methods of separation and purification employed in organic chemistry.

The acetylenic derivatives of formula (I) obtained by the process of the present invention are particularly useful intermediates in organic synthesis and more especially in the synthesis of vitamins A and E.

The products of very particular interest are those of formula (I) in which $R_1$ denotes a radical of formula (II)

in which R₄ denotes a hydroxy radical, R₂ denotes a methyl radical, R₃ denotes an alkyl radical containing 1 to 6 carbon atoms or an alkenyl radical containing 3 to 6 carbon atoms unsubstituted or substituted by a (2,6,6-trimethyl-1-cyclohexenyl)ethenyl radical or R₂ and R₃ together form a 2,6,6-trimethyl-cyclohexyl radical, R₅ denotes a methyl radical, and R₆ denotes a saturated aliphatic radical containing 1 to 10 carbon atoms or an unsaturated aliphatic radical containing 2 to 10 carbon atoms and one or more double bonds, preferably two double bonds in a 1,3-position, unsubstituted or substituted by acetyl, formyl which may be in the form of an acetal radical, or hydroxy which may be in the form of an ether or ester.

Compounds of formula (I) in which R₆ denotes an unsaturated aliphatic radical containing a terminal 1,3-diene radical may be rendered functional for subsequent use under the conditions described in European Patent No. 44,771 by the reaction with a compound containing an active methylene group such as an alkyl acetylacetate.

For example, the condensation of 3-methyl-3-butynol with 3-chloro-6-methylene-2-methyl-1,7-octadiene results in an acetylenic alcohol of formula:

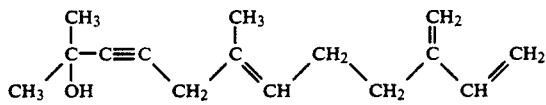

which may be converted into phytone, for example by reaction with methyl acetylacetate under the conditions described in European Patent 44,771, followed by decarboxylation, dehydration and hydrogenation of the product obtained. Phytone may be converted into vitamin E by the application of known methods.

Phytone may be converted into vitamin E, passing through isophytol as an intermediate, in accordance with the process described in Helv. Chim. Acta, 21, 520–525 and 820–825 (1938).

Vitamin E can also be obtained by condensation of trimethylhydroquinone with the product of reaction of 3,7-dimethyl-3-hydroxy-6-octen-1-yne with 6-chloro-3-methylene-7-methyl-1,7-octadiene, followed by dehydration and hydrogenation of the product obtained.

When in the general formula (I) R₆ is a saturated or unsaturated radical substituted by acetyl, formyl which may be in the form of an acetal radical, or hydroxy which may be in the form of an ether or ester, or R₆ is acetyl, formyl which may be in the form of an acetal radical, or hydroxy which may be in the form of an ether or ester, it is possible, depending on the condensation of the carbon atoms of substituents R₁, R₅ and R₆, to prepare geranylacetone, phytone or citral, which are known intermediates for the preparation of vitamin E.

When in the general formula (I), R₁ denotes a radical of general formula (II), in which R₂ denotes a methyl radical, R₃ denotes a (2,6,6-trimethyl-1-cyclohexenyl-)ethenyl radical, R₄ denotes a hydroxy radical, R₅ denotes a methyl radical and R₆ denotes a dimethoxymethyl radical, the corresponding product is of particular interest for access to vitamin A after dehydration and partial hydrogenation.

The following Examples show how the invention may be operated.

EXAMPLE 1

Into a 500 cc round glass flask are introduced in succession, under an argon atmosphere, cuprous iodide (2 g; 10.5 millimoles), triethylamine (200 cc; 1.4 moles), methylbutynol (CH₃)₂C(OH)—C≡CH (73.77 g; 0.877 mole) and 3-chloro-6-methylene-2-methyl-1,7-octadiene (3-chloromyrcene) (36.84 g) analysing at 87% (0.188 mole). The mixture is stirred for 28 hours at 50° C.

After cooling, the triethylamine hydrochloride formed is separated by filtration (29.15 g after drying). Analysis by gas phase chromatography, with an internal standard, of the solution obtained after filtering (221.77 g) shows that the degree of conversion of the 3-chloromyrcene equals 99% and that the yield of product of formula

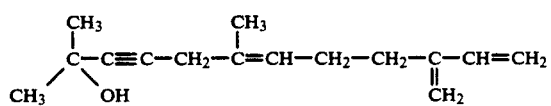

is 83%, based on 3-chloromyrcene employed, with a selectivity of 91%.

The structure of the product obtained (b.p.₀.₂=90° C.) is confirmed by the mass spectrum and by the proton nuclear magnetic resonance spectrum.

EXAMPLE 2

Into a 50 cc round glass flask are introduced successively, under an argon atmosphere, cuprous iodide (94.6 milligrammes; 0.5 millimole), triethylamine (10 cc; 74 millimoles), methylbutynol (3.6 g; 42.8 millimoles) and 3-chloro-1-butene (1.56 g; 17.2 millimoles). The mixture is stirred for 16 hours at 50° C. After filtration of the reaction mixture analysis of the solution obtained by vapour phase chromatography shows that the degree of conversion of 3-chloro-1-butene equals 100% and that the yield of product of formula

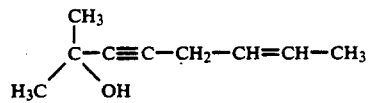

is 85% based on the 3-chloro-1-butene employed.

The structure of the product obtained is confirmed by the mass spectrum and the proton nuclear magnetic resonance spectrum.

EXAMPLE 3

Into a 50 cc round glass flask are introduced in succession, under an argon atmosphere, cuprous iodide (96.8 milligrammes; 0.51 millimole), triethylamine (10 cc; 74 millimoles), methylbutynol (3.63 g; 43.1 millimoles) and 1-bromo-2-butene (2.47 g; 18.2 millimoles).

The mixture is stirred for 16 hours at 50° C. After filtration of the reaction mixture, analysis of the solution obtained by gas phase chromatography shows that the degree of conversion of 1-bromo-2-butene equals 100% and that the yield of product of formula:

$$\underset{CH_3}{\underset{|}{\overset{CH_3}{\overset{|}{C}}}}-C\equiv C-CH_2-CH=CH-CH_3$$
$$\phantom{CH_3}\diagdown OH$$

is 85% based on the 1-bromo-2-butene employed.

EXAMPLE 4

Into a 50 cc round glass flask are introduced in succession, under an argon atmosphere, cuprous iodide (95 milligrammes; 0.5 millimole), triethylamine (10 cc; 74 millimoles), methylbutynol (3.54 g; 42.1 millimoles) and methallyl chloride (1.55 g; 17.1 millimoles).

The mixture is stirred for 16 hours at 50° C. After filtration of the reaction mixture, analysis of the solution obtained by vapour phase chromatography shows that the degree of conversion of methallyl chloride equals 100% and that the yield of product of formula:

$$\underset{CH_3}{\underset{|}{\overset{CH_3}{\overset{|}{C}}}}-C\equiv C-CH_2-\overset{\overset{CH_2}{\|}}{C}-CH_3$$
$$\phantom{CH_3}\diagdown OH$$

equals 100% based on the methallyl chloride employed.

The structure of the product obtained is confirmed by the mass spectrum, the infrared spectrum and the proton nuclear magnetic resonance spectrum.

EXAMPLE 5

Into a 50 cc round glass flask are introduced in succession, under an argon atmosphere, cuprous iodide (0.1 g; 0.52 millimole), triethylamine (20 cc; 148 millimoles), methylbutynol (5.04 g; 60 millimoles) and 1-chloro-2-methyl-4-acetoxy-2-butene (3.25 g; 20 millimoles).

The mixture is stirred for 12 hours at 60° C. A white precipitate of triethylamine hydrochloride forms, and is separated by filtration. The reaction mixture is washed with water and then after decantation the aqueous phase is extracted with ethyl acetate (3×20 cc). The combined organic phases are dried over magnesium sulphate. After filtration and evaporation of the solvent a yellow oil (7.7 g) is obtained, the analysis of which by gas phase chromatography shows the presence of 54% of the product of formula:

$$\underset{CH_3}{\underset{|}{\overset{CH_3}{\overset{|}{C}}}}-C\equiv C-CH_2-\overset{\overset{CH_3}{|}}{C}=CH-CH_2-O-\overset{\overset{}{\|}\,O}{C}-CH_3$$
$$\phantom{CH_3}\diagdown OH$$

The yield is 98% based on 1-chloro-2-methyl-4-acetoxy-2-butene employed.

The structure of the product obtained is confirmed by the mass spectrum and the proton nuclear magnetic resonance spectrum.

EXAMPLE 6

Into a 250 cc round glass flask are introduced in succession under an argon atmosphere, cuprous iodide (0.5 g; 2.6 millimoles), triethylamine (20 cc; 148 millimoles), methylbutynol (10 cc; 103 millimoles), 1-chloromyrcene (1-chloro-2-methyl-6-methylene-2,7-octadiene) (1.49 g; 8.7 millimoles) and 3-chloromyrcene (1 g; 5.8 millimoles). The mixture is stirred for 48 hours at 50° C. After filtration of the reaction mixture, analysis of the solution obtained by gas phase chromatography shows that the degree of conversion of the mixture of 1-chloromyrcene and 3-chloromyrcene equals 97% and that the yield of product obtained, which is identical to that obtained in Example 1, is 66% based on the chloromyrcenes employed. The selectivity is 81%.

EXAMPLE 7

Into a 50 cc round glass flask are introduced in succession, under an argon atmosphere, cuprous iodide (95.3 mg; 0.5 millimole), triethylamine (1.83 g; 18 millimoles), methylbutynol (10 cc; 103 millimoles) and 1-chloro-2-methyl-4,4-dimethoxy-2-butene (2.60 g; 15.8 millimoles).

The mixture is stirred for 16 hours at 60° C. After filtration of the reaction mixture and removal of the volatile products, an oil (6.22 g) is obtained the analysis of which by vapour phase chromatography shows that the degree of conversion of 1-chloro-4,4-dimethoxy-2-methyl-2-butene equals 68% and that the yield of product of formula:

$$\underset{CH_3}{\underset{|}{\overset{CH_3}{\overset{|}{C}}}}-C\equiv C-CH_2-\overset{\overset{CH_3}{|}}{C}=CH-CH\overset{\diagup OCH_3}{\diagdown OCH_3}$$
$$\phantom{CH_3}\diagdown OH$$

is 60% based on the 1-chloro-4,4-dimethoxy-2-methyl-butene employed. The selectivity is 95%.

EXAMPLE 8

Into a 250 cc round glass flask are introduced in succession, under an argon atmosphere, cuprous iodide (0.2 g; 1 millimole), triethylamine (30 cc; 0.22 mole), methylbutynol (7 cc; 72.3 millimoles) and a mixture (11 g) containing geranylacetone (5.5 g) and 3-chlorogeranylacetone (3-chloro-2,6-dimethyl-10-oxo-1,6-undecadiene) (5.5 g; 24 millimoles).

The mixture is stirred for 16 hours at 50° C. After filtration of the reaction mixture, analysis by gas phase chromatography shows that the degree of conversion of 3-chlorogeranylacetone equals 100% and that the yield of product of formula $$\underset{HO}{\underset{\diagup}{\overset{CH_3}{\overset{|}{C}}}}\underset{CH_3}{\diagdown}-C\equiv C-CH_2\underset{}{\overset{\overset{CH_3}{|}}{C}}=CH{+}CH_2{\overline{)_2}}\overset{\overset{CH_3}{|}}{C}=CH-CH_2-CH_2-\overset{\overset{O}{\|}}{C}-CH_3$$

is 85% based on the 3-chlorogeranylacetone employed.

The structure of the product obtained is confirmed by the proton nuclear magnetic resonance spectrum, the mass spectrum and the infrared spectrum.

EXAMPLE 9

Into a 50 cc round glass flask are introduced in succession, under an argon atmosphere, cuprous iodide (19 mg; 0.1 millimole), triethylamine (10 cc; 74 millimoles), phenylacetylene (3.06 g; 30 millimoles) and 3-chloromyrcene (1.70 g; 10 millimoles).

The mixture is stirred for 8 hours at 80° C. After filtration of the reaction mixture, analysis by vapour phase chromatography shows that the degree of conversion of 3-chloromyrcene equals 100% and that the yield of product of formula:

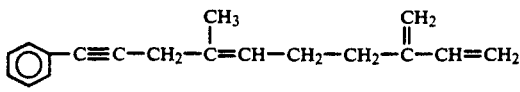

is 72% based on the 3-chloromyrcene employed. The selectivily is 87%.

The structure of the product obtained is confirmed by the proton nuclear magnetic resonance spectrum.

EXAMPLE 10

Into a 100 cc round glass flask are introduced in succession, under an argon atmosphere, cuprous chloride (10 mg; 0.1 millimole), potassium iodide (0.1 g; 0.6 millimole), triethylamine (20 cc; 148 millimoles), methylbutynyl (5.04 g; 60 millimoles) and 3-chloromyrcene (3.41 g; 20 millimoles).

The mixture is stirred for 16 hours at 60° C. After filtration of the reaction mixture, analysis by gas phase chromatography shows that the degree of conversion of 3-chloromyrcene equals 98.7% and that the yield of a product which is identical to that obtained in Example 1 equals 68% based on the 3-chloromyrcene involved. The selectivity is 87%.

EXAMPLE 11

Into a 100 cc round flask are introduced in succession, under an argon atmosphere, cuprous iodide (0.5 g; 2.6 millimoles), triethylamine (40 cc; 296 millimoles), dehydrolinalol [(CH$_3$)$_2$C=CH$_2$—C(CH$_3$)(OH)—C≡CH)] 15.3 g; 0.1 mole) and 3-chloromyrcene (8.52 g; 50 millimoles).

The mixture is stirred for 72 hours at 50° C.

A white precipitate of triethylamine hydrochloride is seen to form. After filtration, an oil (17 g) is obtained the analysis of which by gas phase chromatography shows that the degree of conversion of dehydrolinalol equals 32% and that the yield of product of formula:

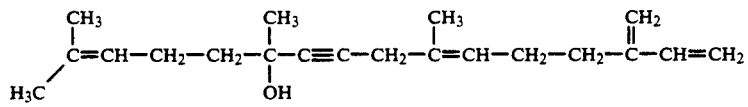

is 31.4% based on the dehydrolinalol employed.

The selectivity is 85%.

The structure of the product obtained is confirmed by the infrared spectrum and by the proton nuclear magnetic resonance spectrum.

EXAMPLE 12

Into a 100 cc round glass flask are introduced in succession, under an argon atmosphere, anhydrous cuprous chloride (0.134 g; 1 millimole), triethylamine (30 cc; 222 millimoles), methylbutynol (5.04 g; 60 millimoles) and 3-chloromyrcene (3.40 g; 20 millimoles).

The mixture is stirred for 64 hours at 50° C. After removal of triethylamine hydrochloride by filtration and concentration under reduced pressure, a product of formula:

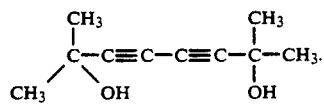

(0.92 g; 0.55 millimole), formed during the reduction of cupric chloride to cuprous chloride which catalyses the reaction, is isolated.

Analysis of the reaction mixture by gas phase chromatography shows that the degree of conversion of 3-chloromyrcene equals 77% and the yield of a product which is identical to that obtained in Example 1 equals 65.7% based on the 3-chloromyrcene involved.

The selectivity is 85.3%.

EXAMPLE 13

Into a 100 cc round glass flask are introduced in succession, under an argon atmosphere, cuprous iodide (0.5 g; 2.62 millimoles), triethylamine (60 cc; 0.44 mole), 1-ethynyl-1-hydroxy-2,2,6-trimethylcyclohexane (16.6 g; 0.1 mole) and 3-chloromyrcene (8.52 g; 50 millimoles).

The mixture is stirred for 48 hours at 50° C. After filtration of the reaction mixture, analysis by gas phase chromatography shows that the yield of product of formula:

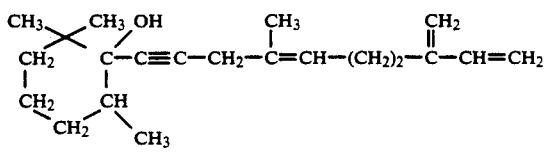

is 33% based on the 3-chloromyrcene employed.

The selectivity is 95%.

The structure of the product obtained is confirmed by the mass spectrum, the infrared spectrum and the proton nuclear magnetic resonance spectrum.

EXAMPLE 14

Into a 250 cc round glass flask are introduced in succession, under an argon atmosphere, cuprous iodide (0.4 g; 2.1 millimoles), triethylamine (30 cc; 222 millimoles), ethynyl β-ionol (4.7 g; 21.5 millimoles) and methallyl chloride (21.16 g; 0.23 mole).

The mixture is stirred for 40 hours at 50° C. After filtration of the reaction mixture, analysis by gas phase chromatography shows that the degree of conversion of ethyl β-ionol equals 83% and that the yield of product of formula

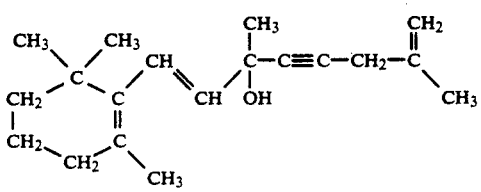

is 56.7% based on the ethyl β-ionol employed.

The structure of the product obtained is confirmed by the proton nuclear magnetic resonance spectrum.

EXAMPLE 15

Into a 160 cc round glass flask are introduced in succession, under an argon atmosphere, [CuCl(1,5-cyclooctadiene)]$_2$ (0.445 g i.e. 2.18 milligramme-atoms of Cu), triethylamine (40 cc; 285 millimoles) and 3-chloromyrcene analysing at 83% (7.90 g; 38.6 millimoles). The mixture is heated to 60° C. over 1 hour and methylbutynol (15.02 g; 192 millimoles) is then added. The temperature is maintained at 60° C., with stirring, for 6 hours 30 minutes. A white precipitate of triethylamine hydrochlorine is seen to form, which is removed by filtration.

Analysis by gas phase chromatography shows that the degree of conversion of 3-chloromyrcene equals 99.7% and that the yield of a product which is identical to that obtained in Example 1 is 79.4% based on the 3-chloromyrcene employed. The selectivity is 88%.

EXAMPLE 16

Into a 160 cc glass reactor fitted with stainless steel baffles and a turbine stirrer, are added in succession, under an argon atmosphere, [RhCl(1,5-cyclooctadiene)]$_2$ (83.4 milligrammes; 0.34 milligramme-atom of rhodium), sodium salt of meta-trisulphonated triphenylphosphine (2.12 g; 3.4 milligramme-atoms of p+$^3$) Na$_2$CO$_3$ (0.161 g), distilled water (34 cc), methanol (4 cc), methyl acetylacetate (26.82 g; 0.231 mole) and the product obtained in Example 1 (32.97 g; 0.151 mole).

The reaction mixture is stirred for 6 hours at 80° C. After cooling and decantation, a liquid (51.14 g) is obtained, containing an equimolar mixture (46.92 g) of products of formula

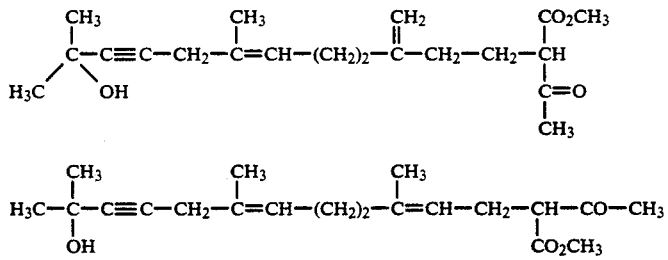

The degree of conversion of the product obtained in Example 1 equals 98.7% and that of methyl acetylacetate equals 64%.

The yield based on the product obtained in Example 1 employed equals 93%. The selectivity is 94.3%.

Into a 500 cc round glass flask fitted with a magnetic stirrer are introduced, under an argon atmosphere, the mixture obtained above, analysing at 91.4% (43.65 g; 0.12 mole), water (100 cc) and caustic soda liquor (30.75%, 17.2 g; 0.132 mole). Stirring is maintained for 16 hours at 20° C. Sulphuric acid (7.11 g diluted with water (25 cc) is then added. Decarboxylation takes place starting at 20° C. and an organic layer is formed which is separated by decantation. A mixture (33 g) of products of formula:

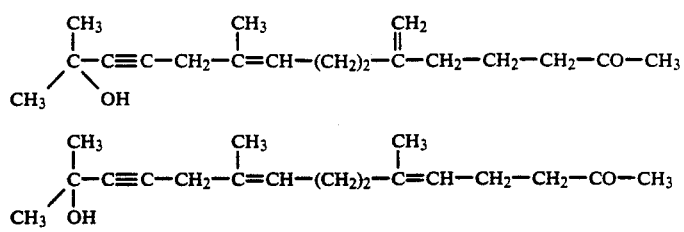

is recovered.

The yield is 99%.

Into a 100 cc round glass flask fitted with a device which permits distillation are introduced, under an argon atmosphere, the mixture obtained above (12.03 g; 43.6 millimoles), toluene (50 cc) and sulphuric acid (0.11 g). The mixture is heated to reflux for 30 minutes, the water formed during the dehydration being removed. After cooling, sodium bicarbonate (0.2 g; 1.9 millimole) is added and the mixture is left to react for 16 hours. The toluene solution is then filtered and put in a stainless steel autoclave containing 10% Pd/C (0.5 g). The autoclave is heated to 50° C. and held under a hydrogen pressure of 3 bars for 8 hours.

After removal of the catalyst by filtration and evaporation of the solvent a liquid (11.5 g analysing for 98% phytone is recovered. The yield equals 96.5% based on the dehydrated product employed.

The structure of phytone is confirmed by the $^{13}$C nuclear magnetic resonance spectrum and the mass spectrum.

EXAMPLE 17

Into a 50 cc round glass flask are introduced in succession, under an argon atmosphere, cuprous iodide (97.4 mg; 0.51 millimole), triethylamine (10 cc; 73.6 millimoles), methylbutynyl acetate

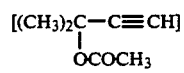

(5.30 g; 42 millimoles) and 3-chloromyrcene analysing at 83.4% (3 g; 14.7 millimoles).

The reaction mixture is stirred for 48 hours at 50° C. After removal of triethylamine hydrochloride by filtration and treatment with water, a liquid (3.94 g) containing the product of formula:

$$CH_3\diagdown\atop{CH_3\diagup}C-C\equiv C-CH_2-\underset{OCOCH_3}{\overset{CH_3}{\underset{|}{C}}}=CH-(CH_2)_2-\overset{CH_2}{\underset{\|}{C}}-CH=CH_2$$

is recovered.

EXAMPLE 18

Into a 50 cc round glass flask are introduced in succession, under an argon atmosphere, cuprous iodide (95.9 mg; 0.50 millimole), triethylamine (10 cc; 73.4 millimoles), methylbutynol (3.6 g; 42.8 millimoles) and an equimolar mixture (3.5 g; 15.3 millimoles) of 2-methyl-3-chloro-6-methylene-10-oxo-1-undecene and 3-chlorogeranylacetone.

The mixture is stirred for 72 hours at 60° C. After removal by filtration of the triethylamine hydrochloride formed and treatment with water, a mixture containing products of formula $$CH_3\diagdown\atop{CH_3\diagup}\underset{OH}{\overset{|}{C}}-C\equiv C-CH_2-\overset{CH_3}{\underset{|}{C}}=CH(CH_2)_2-\overset{CH_2}{\underset{\|}{C}}-CH_2-CH_2-CH_2-CO-CH_3$$

$$CH_3\diagdown\atop{CH_3\diagup}\underset{OH}{\overset{|}{C}}-C\equiv C-CH_2-\overset{CH_3}{\underset{|}{C}}-CH(CH_2)_2-\overset{CH_3}{\underset{|}{C}}=CH-CH_2-CH_2-CO-CH_3$$

(3.11 g) is recovered.
The yield is 73.6%.

EXAMPLE 19

Into a 160 cc glass reactor with central stirring provided by a turbine are introduced in succession, under an argon atmosphere, cuprous iodide (0.401 g; 2.1 millimoles), triethylamine (40 cc; 0.285 mole), 3-chloromyrcene analysing at 83.4% (7.74 g; 37.9 millimoles). The reaction mixture is heated to 60° C. with stirring and then methylbutynol (15.02 g; 178 millimoles) is added over 5 minutes.

The mixture is held at 60° C. for 23 hours.

The degree of conversion of 3-chloromyrcene equals 100% and the yield of a product which is identical to that obtained in Example 1 is 81.5% based on the 3-chloromyrcene employed.

the selectivity is 87%.

EXAMPLE 20

Into a 1.3 litre glass reactor with central stirring provided by a turbine are added in succession, under an argon atmosphere, cuprous chloride (4.0116 g; 40.5 millimoles), triethylamine (740 cc; 5.284 moles) and 3-chloromyrcene analysing at 84.8% (183.38 g; 0.914 mole). The mixture is heated to 53.5° C. with stirring and then methylbutynol (255.31 g; 3.035 moles) is added over 30 minutes.

The mixture is held at 60° C. for 22 hours.

The degree of conversion of 3-chloromyrcene equals 100% and the yield of a product which is identical to that obtained in Example 1 is 81% based on the 3-chloromyrcene involved.

The selectivity is 87%.

EXAMPLE 21

Into a 250 cc round glass flask are introduced in succession, under an argon atmosphere, Cu$_2$O (0.15 g; 1.04 millimole), triethylamine (40 cc; 0.285 mole) and 3-chloromyrcene analysing at 83.4% (7.43 g; 36.3 millimoles).

The mixture is heated to 60° C. over 30 minutes with stirring and then methylbutynol (14.81 g; 0.176 mole) is added over 5 minutes. The mixture is held at 60° C. for 9 hours.

The degree of conversion of 3-chloromyrcene equals 98.1% and the yield of product identical to that obtained in Example 1 is 74.7% based on the 3-chloromyrcene employed.

The selectivity is 89.2%.

EXAMPLE 22

Into a 0.4 liter glass reactor with central stirring provided by a turbine are introduced in succession, under an argon atmosphere, cuprous chloride (2.11 g; 21.3 millimoles), triethylamine (200 cc; 1.39 mole) and 3-chloromyrcene analysing at 95% (15.45 g; 0.42 mole).

The mixture is heated to 60° C. with stirring, and methylbutynol (37.47 g; 0.445 mole) is then run in over 10 minutes. The mixture is held at 60° C. for 9 hours.

After removal of triethylamine hydrochloride formed by filtration and washing of the precipitate with triethylamine, an organic solution (193.28 g) is recovered.

The degree of conversion of 3-chloromyrcene equals 92.6% and the yield of product identical to that obtained in Example 1 is 80.2% based on the 3-chloromyrcene involved.

The selectivity is 87.1%.

EXAMPLE 23

Into a 250 cc round glass flask are introduced in succession, under an argon atmosphere, cuprous iodide (0.788 g; 4.1 millimoles), triethylamine (50 cc; 368 millimoles), a 35-65 mixture (21.96 g) of 3-chloro-2,6-dimethyl-9-carbomethoxy-1,6-undecadien-10-one and of 3-chloro-2-methyl-6-methylene-9-carbomethoxy-1-undecen-10-one (76.6 millimoles) and methylbutynol (14.02 g; 167 millimoles). The reaction mixture is stirred at 60° C. for 20 hours. After filtration of the reaction mixture to remove triethylamine hydrochloride and concentration, an oil (30.12 g) containing a mixture of products of the formula:

$$(CH_3)_2C(OH)-C\equiv C-CH_2-C(CH_3)=CH-(CH_2)_2-\overset{CH_2}{\underset{\|}{C}}-CH_2CH_2-CH(COCH_3)COOCH_3$$

and

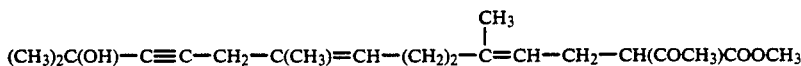

is recovered.

The degree of conversion of the product employed equals 100%.

EXAMPLE 24

Into a 400 cc glass reactor fitted with central stirring provided by a turbine are introduced, under an argon atmosphere, cuprous chloride (1.98 g; 20 millimoles), potassium chloride (1.495 g; 20 millimoles), triethylamine (200 cc; 1.39 moles) and 3-chloro-6-methylene-2-methyl-1,7-octadiene (3-chloromyrcene) analysing at 92% (76.37 g i.e. 0.413 mole).

The mixture is heated to 60° C. with stirring, and methylbutynol (37.52 g; 0.446 mole) is then added over 10 minutes. The mixture is held at 60° C. for 18 hours.

After cooling to 20° C., the triethylamine hydrochloride formed is separated by filtration and is washed with acetone (150 cc). The dry precipitate weighs 39.7 g and contains 3.6 mg of copper.

The filtrate obtained weighs 266.88 g.

Analysis of this filtrate shows that the degree of conversion of 3-chloromyrcene is 100% and that the yield of product of formula:

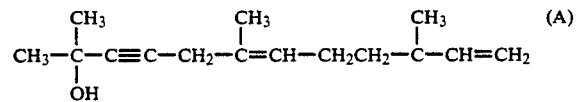

is 69.4% based on the 3-chloromyrcene employed. The selectivity is 88%.

The filtrate is concentrated under reduced pressure (20 mm Hg; 2.7 kpa) at 40° C. A red oil (115.5 g) is thus obtained, analysis of which shows that it contains copper (1.270 g; 1.1%) and the condensation product (A) (62.1 g).

This oil is stirred with hexane (500 cc) for 30 minutes and then left to separate for 1 hour.

A hexane extract (336.13 g) is thus obtained containing the condensation product (A) (34.06 g) and copper (0.144 g).

The raffinate is treated with hexane (250 cc) for 30 minutes and left to separate for 1 hour.

A hexane extract (181.6 g) is obtained containing condensation product (A) (9.28 g) and copper (0.009 g).

The raffinate is treated with hexane (250 cc) for 30 minutes and left to separate for 1 hour.

A hexane extract (170.22 g) is obtained containing condensation product (A) (5.37 g) and containing no copper.

The raffinate is again treated with hexane (250 cc) for 30 minutes and left to separate for 1 hour.

A hexane extract (162.57 g) is thus obtained containing condensation product (A) (4.1 g).

The raffinate finally obtained (34.65 g), which contains condensation product (A) (7.84 g) and copper (1.019 g), may be employed in a subsequent condensation 80% of the copper employed is thus recovered.

Condensation product (A) (52.81 g) is obtained by concentrating the hexane extracts.

EXAMPLE 25

Into a 160 cc glass reactor fitted with central stirring provided by a turbine are introduced in succession, under an argon atmosphere, cuprous chloride (0.203 g; 2 millimoles), triethylamine (20 cc; 145 millimoles) and a 45/55 mixture (12.14 g) of 3-chloro-2,6-dimethyl-9-carbomethoxy-1,6-undecadien-10-one and of 3-chloro-2-methyl-6-methylene-9-carbomethoxy-1-undecen-10-one analysing for 85% by weight (i.e. 36 millimoles).

The reaction mixture is heated to 60° C. with stirring, and methylbutynol (3.72 g; 44.2 millimoles) is then added over 1 minute. The reaction mixture is held at 60° C. for 23 hours.

After cooling to 20° C., triethylamine hydrochloride is separated by filtration and is washed with acetone (30 cc).

The dry precipitate weighs 3.91 g and contains copper (0.72 mg).

The filtrate obtained weighs 57.86 g.

Analysis of the filtrate shows that the degree of conversion of the chlorinated products employed is 100% and that the yield of condensation products consisting of a 45/55 mixture of;

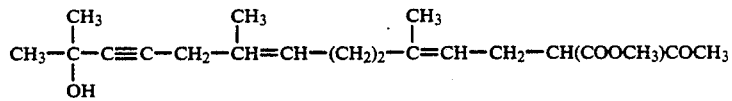

and

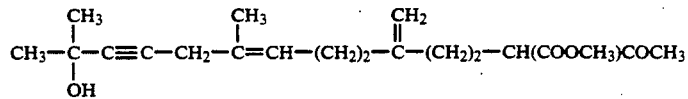

is 78.9% based on the chlorinated products employed. The selectivity is 95%.

The filtrate is concentrated under reduced pressure (20 mm Hg; 2.7 kPa) at 40° C. A red oil (15.54 g) is thus obtained, containing condensation products (9.5 g) and copper (0.124 g).

The oil is extracted 6 times in succession with ethyl ether after separating for 1 hour each time.

The results of the successive extractions are collated in the following table:

| Extraction no. | Ethyl ether (cc) | Stirring time (h) | Composition of the ether extract after concentration | |
|---|---|---|---|---|
| | | | Product (g) | Copper (g) |
| 1 | 60 | ¾ | 8.22 | 0.015 |
| 2 | 50 | ¾ | 0.79 | |
| 3 | 40 | 1¼ | 0.46 | |
| 4 | 40 | 1¼ | 0.1 | |
| 5 | 40 | 2 | 0 | |
| 6 | 40 | 2 | 0.05 | |

The raffinate finally obtained, which contains condensation products (5.11 g) and copper (0.114 g), may be employed in a subsequent condensation operation.

89.7% of copper employed is thus recovered.

EXAMPLE 26

Into a 160 cc glass reactor fitted with central stirring provided by a turbine are introduced in succession, under an argon atmosphere, cuprous chloride (0.8 g; 8.08 millimoles), triethylamine (80 cc; 0.58 mole) and a 45/55 mixture (45.90 g) of 3-chloro-2,6-dimethyl-9-carbomethoxy-1,6-undecadien-10-one and of 3-chloro-2-methyl-6-methylene-9-carbomethoxy-1-undecen-10-one analysing at 82% by weight (i.e. 131.4 millimoles). The reaction mixture is heated to 60° C., and methylbutynol (13.25 g; 157.5 millimoles) is then added over 1 minute. The reaction mixture is held at 60° C. with stirring for 23 hours.

After cooling to 20° C., triethyl hydrochloride is separated by filtration and is washed with acetone (140 cc).

The dry precipitate weighs 13.63 g and contains copper (2.6 mg).

The filtrate, after concentration at 40° C. under reduced pressure (20 mm Hg; 2.7 kPa), weighs 54.19 g and contains copper (0.488 g).

The degree of conversion of the chlorinated products employed is 100% and the yield of condensation products (which are identical to those obtained in Example 25) is 75.4% based on the chlorinated products employed. The selectivity is 95%.

The filtrate is repeatedly extracted with ethyl ether (2×200 cc) after separating for 1 hour each time.

Finally a raffinate is obtained which contains condensation products (14.18 g) and copper (0.475 g) and which may be employed directly in a subsequent operation.

89.7% of the copper employed is thus recovered.

The ether phases, after being concentrated, yield the condensation products (39.86 g).

EXAMPLE 27

Into a 50 cc round glass flask fitted with a magnetic stirrer are introduced in succession, under an argon atmosphere, the raffinate obtained in Example 26 (1.9 g) containing 1 milligramme-atom of copper, triethylamine (10 cc; 72.5 millimoles), a 45/55 mixture (5.72 g) of 3-chloro-2,6-dimethyl-9-carbomethoxy-1,6-undecadien-10-one and of 3-chloro-2-methyl-6-methylene-9-carbomethoxy-1-undecen-10-one analysing for 82% by weight (i.e. 16.37 millimoles), and methylbutynol (1.74 g; 20.7 millimoles).

The reaction mixture is stirred at 60° C. for 23 hours.

After cooling to 20° C., acetone (20 cc) is added and triethylamine hydrochloride is removed by filtration. The dry precipitate weights 1.11 g.

The filtrate, after concentration at 40° C. under reduced pressure (20 mm Hg; 2.7 kPa), weights 8.5 g.

Analysis of the concentrated filtrate shows that the degree of conversion of the chlorinated products employed is 39.6% and that the yield of condensation products is 18.8% based on the chlorinated products employed. The selectivity is 95%.

After treatment of the filtrate with ethyl ether under the conditions described in Example 26, an ether phase is obtained which yields the condensation products (3.72 g).

We claim:

1. A process for preparing an acetylenic derivative of formula:

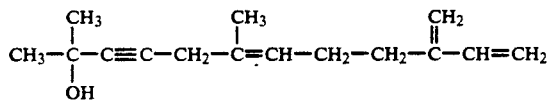

by reacting methylbutynol with a mixture of chloro-3 myrcene and chloro-1 myrcene in the presence of a catalyst consisting essentially of a copper derivative in a quantity from 1 to 5 mole % of the said chloromyrcene in the presence of triethylamine in an amount of 100 to 2000 moles % of the chloromyrcene mixture.

* * * * *